United States Patent [19]

Mori

[11] Patent Number: 6,011,135
[45] Date of Patent: Jan. 4, 2000

[54] TRIAZINE THIOL DERIVATIVE HAVING A PERFLUORO GROUP, METHOD FOR PRODUCING SAME AND USE OF SAME

[75] Inventor: Kunio Mori, Morioka, Japan

[73] Assignee: Iwate University, Morioka, Japan

[21] Appl. No.: 09/141,337

[22] Filed: Aug. 27, 1998

[30] Foreign Application Priority Data

Aug. 27, 1997 [JP] Japan .................................. 9-231064

[51] Int. Cl.[7] .................................................. C08G 73/56
[52] U.S. Cl. ........................ 528/423; 528/422; 528/373; 528/374; 528/401
[58] Field of Search .................................... 528/423, 422, 528/373, 374, 401

[56] References Cited

FOREIGN PATENT DOCUMENTS 5-23645  2/1993  Japan .
6-322595  11/1994  Japan .

OTHER PUBLICATIONS

Chem Abstract 129: 246667 "Triazinedithio derivatives capable of forming tridimensional intermolecular bonding and surface treatment using the same for enhanced durability. ""Mori et al."

Kunio Mori et al., "Study on Functionalization of Metal Surfaces. III. Photopolymerization of Monomer Films on Metal Surfaces", *J. Polymer Science: Part A: Polymer Chemistry*, vol. 25, 2893–2907 (1987).

Chemical Abstracts, vol. 121, No. 9, Abstract No. 108712q (Aug. 29, 1994).

H. Baba et al., "The Corrosion Inhibition of Copper by Potentiostatic Anodization in Triazinedithiol Solutions", *Corrosion Science*, vol. 39, No. 3, pp. 555–564 (Mar. 1997).

Derwent Publications, Ltd. Week 9506, Abstract No. 95–041756 (English language) of JP 06 322595.

*Primary Examiner*—Duc Truong
*Attorney, Agent, or Firm*—Venable

[57] ABSTRACT

The triazine thiol derivative having a perfluoro group of the present invention is represented by the following chemical formula:

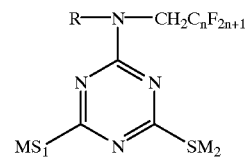

in which "n" is an integer of 1–12, "R" is represented by the following general formula;

$C_mH_{2m+1}$ wherein m is an integer of 0–24, and $M_1$ and $M_2$ respectively represent H or an alkali metal. Such triazine thiol derivative having a perfluoro group is excellent in reactivity, solubility and surface activity.

4 Claims, No Drawings

TRIAZINE THIOL DERIVATIVE HAVING A PERFLUORO GROUP, METHOD FOR PRODUCING SAME AND USE OF SAME

BACKGROUND OF THE INVENTION

1. Field of the Invention

The present invention relates to a novel triazine thiol derivative having a perfluoro group, a method for producing the triazine thiol derivative, and a film for metal surface which is obtained by subjecting a metal to a surface treatment with use of the triazine thiol derivative.

2. Description of the Related Art

Triazine thiol derivatives have already been industrially manufactured (by some manufacturers such as Sankyo Kasei Co. Ltd.) and used as crosslinking agents, adhesion accelerating agents, surface treatments, heavy metal treatments, anti-corrosive agents and the like. Among them, those triazine thiol derivatives whose substituent in 6 place is selected from the group consisting of —SH, —N($C_4H_9$)$_2$, —NHC$_6$H$_5$ and metal salts thereof have been especially used as surface treatments for metals and partly put to practical use (for example, "Practical Surface Treatment Techniques" by Mr. Ikuo Mori, 35, 595 (1988), "Chemical Industry" 42, 1005 (1991)). Although films of conventional triazine thiol derivatives provided on a surface of solid material such as a metal had large surface free energy, thereby attaining improved adhesion property, such conventional films were poor in anti-staining property, non-tackiness, anti-fogging property, lubricity and anti-icing performance.

To solve the above-mentioned problems, Japanese Patent Application Laid-Open No. 6-322595 discloses a method of manufacturing a metal material in which triazine thiol compounds having perfluoro octyl anilino group are electrodeposited on a solid material such as a metal by means of electrolytic polymerizing treatment, so that water repellency is imparted to the metal.

However, the triazine rings of the above-mentioned compounds are coupled by aromatic anilino group and thus, it has large cohesive force while being an electron attractive group. Accordingly, the compounds are poor in solubility, low in reactivity of thiol group and further, critical micelle concentration (surface activity) of the compounds is high. As a result, the above-mentioned compounds cannot perform the functions as a surface treatment agent for metals sufficiently, thereby greatly narrowing the range of its practical use in industrial fields.

SUMMARY OF THE INVENTION

Under the circumstances stated above, the inventor has made various studies in order to solve the above problems and to attain a compound having a novel molecular structure. As a result thereof, the present invention has been accomplished.

It is, therefore, an object of the present invention to provide a triazine thiol derivative having a perfluoro group, which is excellent in reactivity, solubility and surface activity so that it can impart properties such as anti-staining property, nontackiness, anti-fogging property, release property, lubricity and anti-icing property to a metal surface.

Another object of the present invention is to provide a method for efficiently and economically producing such triazine thiol derivative having a perfluoro group.

Still another object of the present invention is to provide a polymerized film of such triazine thiol derivative having a perfluoro group which is formed on a metal surface by a dipping method, tribological method, or electrolytic polymerization method.

To accomplish the above-mentioned objects, there is provided according to the present invention, a triazine thiol derivative having a perfluoro group represented by the following chemical formula (1):

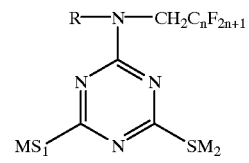

wherein "n" is an integer of 1–12, "R" is represented by the following general formula;

$C_mH_{2m+1}$ wherein m is an integer of 0–24, and $M_1$ and $M_2$ respectively represent a hydrogen atom (H) or an alkali metal.

The present invention also provides a method for producing a triazine thiol derivative having a perfluoro group comprising preparation steps of:

(1) synthesizing a secondary amine having a perfluoro group;
(2) synthesizing a triazine dichloride having a perfluoro group from the secondary amine having a perfluoro group and a cyanur chloride; and then
(3) synthesizing a triazine thiol derivative having a perfluoro group from the triazine dichloride having a perfluoro group.

In such method for producing a triazine thiol derivative having a perfluoro group, the secondary amine having a perfluoro group may be prepared through a reaction represented by the following reaction formula (2);

(1-1)
(1-2)
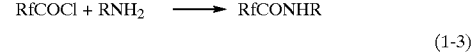
(1-3)

the triazine dichloride having a perfluoro group may be prepared through a reaction represented by the following reaction formula (3);

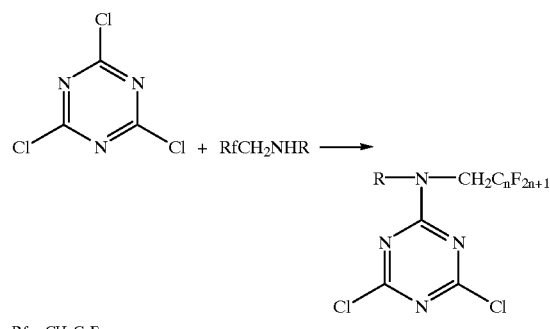

and the triazine thiol derivative having a perfluoro group may be prepared through a reaction represented by the following reaction formula (4);

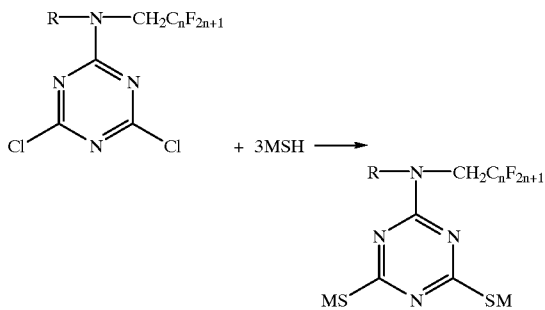

The present invention further provides a film for metal surface comprising the triazine thiol derivative having a perfluoro group.

DETAILED DESCRIPTION OF THE PREFERRED EMBODIMENTS

The present invention will be described in detail with reference to preferred embodiments.

A triazine thiol derivative having a perfluoro group according to the present invention is represented by the following chemical formula (1):

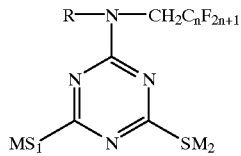

In the above formula, "R" is represented by the following general formula;

$C_mH_{2m+1}$ wherein m is an integer of 0–24, and depending on the purpose of use, "R" may be longer or shorter than the perfluoro group. Especially in the case where "R" is $-C_3H_7$, $-C_4H_9$, $-C_{12}H_{25}$ or $-C_{18}H_{37}$, the resulting product is often excellent in solubility. When "R" is longer than the perfluoro group, the resulting product effectively functions in such case where a polymeric material of fluorocarbon and olefin are miscibilized in the interface. On the other hand, when "R" is shorter than the perfluoro group, the resulting triazine thiol derivative is suitable for treatments such a surface treatment agent which are required to display the properties of fluorine.

In the perfluoro group $-CH_2C_nF_{2+1}$ in the above-mentioned formula (1) in which "n" is an integer of 1–12, the amount of "n" influences the display of fluorine properties. The "n" may preferably be an integer between 1 to 12 from the view point of the balance between fluorine properties and solubility. Among them, $-CH_2C_9F_{19}$ is especially effective. When the perfluoro group is shorter than the above-mentioned range, the properties of fluorine cannot be displayed sufficiently. On the other hand, when the amount of "n" is larger than the above range, the resulting product involves such problems that solubility of raw materials decreases and synthesis of materials becomes difficult in spite of increased display of fluorine properties.

When $M_1$ and $M_2$ in the above formula (1) are respectively an H (in this case, the substance may be referred to as a triazine thiol having a perfluoro group), the triazine thiol having a perfluoro group may be effectively used when it is dissolved in an organic solvent such as tetrahydrofuran, dimethylformamide, glycols, pyrolidone, dimethyl sulfoxide, ketons and the like.

In the case where both or either of $M_1$ and $M_2$ in the above formula (1) is an alkali metal, for example both or either of $M_1$ and $M_2$ is Li, Na, K or Ce, the triazine thiol derivative having a perfluoro group is dissolved in water, alcohol, or a mixed solvent thereof for the practical use.

When both or either of $M_1$ and $M_2$ in the above formula (1) is an ammonia or an amine such as ethanolamines, alkylamines and the like, the resulting triazine thiol derivative having a perfluoro group is used in the form of paste.

The above-described triazine thiol derivative having a perfluoro group according to the present invention is excellent in reactivity, solubility and surface activity when compared with the conventional fluorinated triazine thiol.

The triazine thiol derivative having a perfluoro group according to the present invention, which is represented by the above-mentioned formula (1), can be produced through the following three steps:

(1) synthesizing a secondary amine having a perfluoro group;
(2) synthesizing a triazine dichloride having a perfluoro group from the secondary amine having a perfluoro group and a cyanur chloride; and then
(3) synthesizing a triazine thiol derivative having a perfluoro group from the triazine dichloride having a perfluoro group.

A typical synthetic reaction of the above-mentioned secondary amine having a perfluoro group is as follows:

$$RfCOOH + SO_2Cl_2 \longrightarrow RfCOCl \quad (1\text{-}1)$$

$$RfCOCl + RNH_2 \longrightarrow RfCONHR \quad (1\text{-}2)$$

$$RfCONHR \longrightarrow RfCH_2NHR \quad (1\text{-}3)$$

wherein Rf is represented by the general formula:

$-CH_2C_nF_{2n+1}$ and n is an integer of 1–12.

For example, a perfluorocarboxylic acid is reacted with $SO_2Cl_2$ under the presence of pyridine to prepare a perfluorocarboxylic chloride (1-1) and then, the thus-obtained perfluorocarboxylic chloride is reacted with ammonia or a primary amine, thereby obtaining a perfluoro carboxylic amide (1-2). In place of the above-mentioned perfluorocarboxylic chloride, a perfluoro carboxylic halide such as a perfluoro carboxylic fluoride or the like. After that, the thus-obtained perfluoro carboxylic amide is reduced in a solvent of ethers, in which $LiAlH_4$, $B_2H_6$, $NaBH_4$, $ZnCl_2$, $CoCl_2$ or the like is coexistent, thereby synthesizing a secondary amine having a perfluoro group (1-3).

Next, a typical reaction between the above-explained secondary amine having a perfluoro group and a cyanur chloride is shown in the formula (3) below:

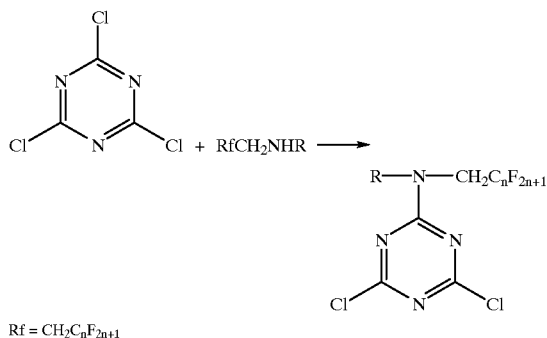

In the reaction represented by the above formula (3), the triazine dichloride having a perfluoro group is obtained as follows. First, a cyanur chloride is dissolved in an organic solvent such as acetone, tetrahydrofuran, dioxane, alcohols, and the like at a temperature of 0° C. or lower, and a solution of the secondary amine having a perfluoro group, which is obtained in the reaction represented by the above formula (2), is dropped thereto. The moment when the solution of the secondary amine having a perfluoro group is dropped, the temperature of the reaction solution increases, whereby the reaction begins. In this connection, the reaction temperature may preferably be maintained within the range of 0–5° C. from the view point of preventing a side reaction. After finishing the dropping of the solution of the secondary amine having a perfluoro group, the reaction solution is stirred for 60 minutes and then, an aqueous solution of $Na_2CO_3$ is dropped thereto. Just like the case when the solution of the secondary amine having a perfluoro group is dropped, it is confirmed that the reaction temperature is raised due to the dropping of $Na_2CO_3$. Also in this case, the reaction temperature should be maintained within the range of 0–5° C. while stirring and dropping are continued. Then, the reaction mixture is poured into water or washed with water after distilling off the solvent, thereby obtaining a crude triazine dichloride having a perfluoro group.

A typical synthetic reaction of a triazine thiol derivative having a perfluoro group is shown in the following formula (4):

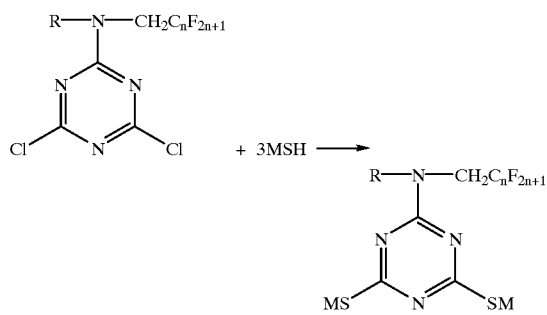

Specifically, the triazine dichloride having a perfluoro group obtained in the above reaction is reacted with a soda hydrosulfide of 3 mol in alcohol or dimethylformamide to attain a triazine thiol derivative having a perfluoro group of the present invention. The above formula (4) represents a typical thiolating method, and a soda sulfide or alkali sulfide may be used in place of a soda hydrosulfide.

Further, an indirect thiolating method can be carried out with use of an alkaline carbamate or an alkali metal xanthate and, through a reaction between the product thereof and a secondary amine, there can be obtained a triazine thiol derivative having a perfluoro group according to the present invention.

The triazine thiol derivative having a perfluoro group according to the present invention may form a film comprising a perfluoro group on a metal surface by a dipping method, tribological method, or electrolytic polymerization method, thereby providing the metal surface with properties such as anti-staining property, non-tackiness, anti-fogging property, lubricity and anti-icing property.

In a dipping method, a film is formed on a metal such as a copper, copper alloy, nickel, iron, aluminum and the like by dipping such metal in an aqueous solution or organic solution of the triazine thiol derivative having a perfluoro group for 0.1–120 minutes, preferably for 3–30 minutes. In this case, the concentration of the solution of the triazine thiol derivative having a perfluoro group is within the range of 0.001–5 weight %, preferably within the range of 0.01–1 weight %. The optimum value of concentration varies depending on the kind of metal to be dipped, dipping temperature and dipping time.

A suitable dipping temperature differs with the concentration of the solution, the kind of metal, especially with the solvent to be used and therefore, it is impossible to specify a single optimum value for the dipping temperature. In the case of an aqueous solution, it can generally vary from 1° C. to 99° C., and desirably the dipping temperature is within the range of 20° C.–80° C. By this dipping method, a uniform film can be formed on a metal product which has a complicated shape. However, the thus-formed film is low in strength because it is a monomer film. Accordingly, after the dipping, the monomer film may be subjected to heating at a temperature of 100° C. or higher, so that it turns into a polymer film. The dipping method described above is especially suitable for a surface treatment of a copper and copper alloy.

In a tribological polymerization method, the triazine thiol derivative having a perfluoro group dissolved or mixed in a water based lubricant or an oil based lubricant, or alternatively, the triazine thiol derivative having a perfluoro group by itself is used as a lubricant during a machining process of a metal such as elongation, cutting, wire drawing and forging, thereby simultaneously conducting the machining and a surface treatment of the metal. Processing machines for elongation, cutting, wire drawing and forging are not limited to particular types as long as they are ordinarily used ones. During the above-mentioned machining processes, the metal momentarily produces a high heat, forms an active new surface and discharges exo-electrons. As a result, the triazine thiol derivative having a perfluoro group in contact with the lubricant are polymerized, thereby forming a film on the metal surface. When the triazine thiol derivative having a perfluoro group of the present invention is dissolved or mixed in a lubricant which is presently available for use, the concentration of resulting dissolution or mixture is generally within a range of 0.001–5 weight %, preferably within a range of 0.01–1 weight %. It is needless to say that even when it is difficult to dissolve the triazine thiol derivative having a perfluoro group in a certain lubricant, the aim also can be accomplished by mixing and slightly dispersing the triazine thiol derivative having a perfluoro group in the lubricant.

In an electrolytic polymerization method, a film of the triazine thiol derivative having a perfluoro group is formed on a surface of a metal or an electric conductor by an electrolytic method such as a cyclic method, a constant-current method, a constant-potential method, a pulse constant-potential method, a pulse constant-current method and the like, wherein an electrolysis is conducted in an aqueous solution or an organic solution of the triazine thiol derivative having a perfluoro group, which also includes an electrolyte, with use of an anode of a metal to be treated and a cathode of a platinum plate or a stainless steel plate. Metals to be treated in this method are not restricted as long as the metals have electrical conductivity. As examples of such metals, mention would be made of iron, iron alloy (such as stainless steel, and permalloy), copper, copper alloy, nickel, gold, silver, platinum, cobalt, aluminum, zinc, lead, tin, tin alloy, titanium, chrome and the like. The above-mentioned electric conductor may include a conductive film, ITO, carbon, conductive rubber, organic conductor and the like.

The above-mentioned electrolyte are not limited to particular materials as long as it has solubility to a solvent used, electric conductivity as well as stability. In general, NaOH, $Na_2CO_3$, $Na_2SO_4$, $K_2SO_3$, $Na_2SO_3$, $K_2SO_3$, $NaNO_2$, $KNO_2$, $NaNO_3$, $NaClO_4$, $CH_3COONa$, $Na_2B_2O_7$, $NaH_2PO_2$, $(NaPO_3)_6$, $Na_2MoO_4$, $Na_3SiO_3$ and the like are suitably used as an electrolyte. The concentration of these electrolyte is generally within a range of 0.001–1 mol/L, preferably within a range of 0.1–0.5 mol/L from the view point of the growth rate of the film.

As the above-described solvent, one which can dissolve an electrolyte and the triazine thiol derivative having a perfluoro group at the same time is desirable and combination of such solvents is not particularly restricted. As examples of such solvent, mention may be made of water, methanol, ethanol, carbitol, Cellosolve, dimethylformamide, methylpyrolidone, acrylnitrile, ethylene carbonate and the like.

The concentration of the triazine thiol derivative having a perfluoro group is within the range of 0.01–100 mmol/L, preferably within the range of 0.1–10 mmol/L. The temperature of the electrolyte differs with the freezing point and boiling point of the solvent used and therefore, it is difficult to specify a single optimum value for the temperature of the electrolyte. For example, in the case of an aqueous solution, the temperature varies from 1° C. to 99° C., but it is within the range of 20° C.–80° C.

As the material for the counter electrode (the cathode), a discretional material can be used as long as it neither reacts with the electrolyte nor has extremely low conductivity. In general, an inactive electric conductor such as a stainless steel, platinum, carbon and the like is used as the counter electrode.

The cyclic method is conducted with such a potential width that the solvent is not decomposed. Such potential width cannot be specifically restricted since it is affected by the kinds of solvent and electrolyte to be used. The constant-potential method is conducted at a potential within the range of −0.5–2 V vs. CES, preferably at a potential within the range from a spontaneous potential to an oxidation potential. When constant-potential method is conducted at a potential lower than the spontaneous potential, there is such a risk that no polymerization occurs. On the other hand, constant-potential method at a potential higher than the oxidation potential takes a risk of decomposition of the solvent.

In the constant-current method, a suitable current density is within the range of 0.005–50 $mA/cm^2$, preferably within the range of 0.05–5 $mA/cm^2$. When the current density is lower than 0.05 $mA/cm^2$, growth of a film takes too long time. When the current density is higher than 5 $mA/cm^2$, there may happen such an undesirable phenomenon that a crack appears in the resulting film or the metal elutes into the electrolyte.

In a pulse method, an electrolytic potential and an electrolytic current density may be decided just as described above, and the duration of electrolysis is within the range of 0.01–10 minutes, preferably within the range of 0.1–2 minutes. When the duration is shorter than 0.01 minute or longer than 10 minutes, the effects of the pulse method cannot be attained sufficiently.

With respect to preliminary treatments of a metal, a foreign substance such as an organic substance should be removed from the metal surface. However, substances such as oxides do not matter as long as they do not considerably deteriorate the conductivity. An activating treatment is not necessary as long as conductivity of the metal is not considerably deteriorated.

The following examples and comparative examples are given in illustration of the present invention and are not intended as limitations thereof.

EXAMPLES 1–10

After adding a perfluoro alkyl carboxylic acid (0.50 mol) and a dimethylformamide (DMF) into hexane (200 ml), a thionyl chloride (1 mol) was dropped thereinto and the resulting solution was heated at reflux for 24 hours. The solvent and the excess of thionyl chloride were removed by means of an evaporator and then, distillation was conducted under a reduced pressure, thereby obtaining a perfluoro alkyl carboxylic chloride. The thus-obtained perfluoro alkyl carboxylic chloride was purified by further conducting the reduced-pressure distillation twice. The yield was 45–89%.

In the case of a perfluoro alkyl carboxylic acid having a carbon number of not more than 4, a phosphorus pentachloride and toluene were used, and the reaction was conducted at 50° C. for 24 hours. An initial distillate obtained by distilling this reaction solution was a perfluoro alkyl carboxylic chloride. The thus-obtained perfluoro alkyl carboxylic chloride was purified by conducting the distillation again. The yield was 45–62%.

Then, a triazine thiol derivative having a perfluoro group was synthesized through the processes represented by formulae (1-1), (1-2) and (1-3) of the chemical formula (2), formula (2-1) of the chemical formula (3) and formula (3-1) of the chemical formula (4).

Characteristic values of a perfluoro alkyl amine, 6-perfluoro alkylamino-1,3,5-triazine-2,4-dichloride and 6-perfluoro alkylamino-1,3,5-triazine-2,4-dithiol obtained in Examples 1–10 are respectively shown in Tables 1–3.

TABLE 1

Characteristic values of perfluoro alkyl amine

| Example | Amine including fluorine | Yield (%) | State | Distillation boiling point (° C./Torr) | Melting point (° C.) | $N^{1)}$ (%) | IR characteristic absorption$^{2)}$ (cm$^{-1}$) |
|---|---|---|---|---|---|---|---|
| 1 | $CF_3(CF_2)CH_2NH_2$ | 84 | colorless/liquid | 49–50/760 | — | 9.4/9.39 | NH: 3312w, 31924w<br>CH: 2958m, 2878m<br>CF: 1209s, 1149s |
| 2 | $CF_3(CF_2)_6CH_2NH_2$ | 53 | colorless/liquid | 79–82/32 | — | 3.6/3.51 | NH: 3312w, 31924w<br>CH: 2958m, 2878m<br>CF: 1209s, 1149s |
| 3 | $CF_3(CF_2)_8CH_2NH_2$ | 45 | colorless/solid | 95–99/15 | 43–44 | 2.7/2.81 | NH: 3420w, 3215w<br>CH: 2952m, 2872m<br>CF: 1245s, 1205s, 1149s |
| 4 | $CF_3(CF_2)_6CH_2NHC_4H_7$ | 72 | colorless/solid | recrystallized | 104–105 | 3.0/3.09 | NH: 3241w, 3216w<br>CH: 2950m, 2871m<br>CF: 1245s, 1204s, 1150s |
| 5 | $CF_3(CF_2)_9CH_2NH_2$ | 79 | colorless/liquid | 39–40/0.3 | — | 2.7/2.55 | NH: 3367w<br>CH: 2966m, 2862m<br>CF: 1242s, 1210s, 1150s |
| 6 | $CF_3(CF_2)_6CH_2NHC_8H_{17}$ | 59 | colorless/liquid | 40–84/0.07 | — | 2.8/2.64 | NH: 3375w<br>CH: 2931m, 2860m<br>CF: 1242s, 1211s, 1150s |
| 7 | $CF_3(CF_2)_6CH_2NHC_{12}H_{25}$ | 74 | colorless/liquid | 113–118/0.07 | — | 2.4/2.47 | NH: 3346w<br>CH: 2928m, 2857m<br>CF: 1243s, 1211s, 1150s |
| 8 | $CF_3(CF_2)_6CH_2NHC_6H_5$ | 93 | colorless/solid | 78–79/0.3 | 41–42 | 3.0/2.95 | NH: 3417w<br>CH: 3058w, 1606m<br>CF: 1232s, 1200s, 1144s |
| 9 | $CF_3(CF_2)_6CH_2NHC_6H_{11}$ | 82 | colorless/liquid | 65–68/0.3 | — | 2.8/2.91 | NH: 3443w<br>CH: 2935m, 2860m<br>CF: 1241s, 1209s, 1150s |
| 10 | $CF_3(CF_2)_9CH_2NHC_4H_7$ | 41 | colorless/liquid | 41–43/0.3 | — | 2.3/2.32 | NH: 33469w<br>CH: 2930m, 2859m<br>CF: 1243s, 1211s, 1150s |

$^{1)}$Analyzed by Kjeldahl method; upper row: observed value; lower row: calculated value
$^{2)}$w: weak peak strength; m: medium peak strength; s: strong peak strength

TABLE 2

Characteristic values of 6-perfluoro alkylamino-1,3,5-triazine-2,4-dichloride

| Example | Substituent in 6 place | Yield (%) | Melting point (° C.) | $N^{1)}$ (%) | $C^{1)}$ (%) | IR characteristic absorption$^{2)}$ (cm$^{-1}$) |
|---|---|---|---|---|---|---|
| 1 | $CF_3(CF_2)CH_2NH$— | 90 | 84–85 | 18.6/18.87 | 23.6/23.87 | NH: 3247w, CH: 2947m<br>—N=N<: 1587s, 1524m<br>CF: 1235s, 1201s, 1144s |
| 2 | $CF_3(CF_2)_6CH_2NH$— | 89 | 89–90 | 10.3/10.24 | 12.8/12.96 | NH: 3286w, CH: 2947m<br>—N=C<: 1596s, 1523m<br>CF: 1209s, 1149s |
| 3 | $CF_3(CF_2)_8CH_2NH$— | 75 | 98—99 | 8.8/8.66 | 10.5/10.95 | NH: 3274w, CH: 3138m<br>—N=C<: 1612s, 1553m<br>CF: 1252s, 1211s, 1150s |
| 4 | $CF_3(CF_2)_9CH_2NH$— | 49 | 102–103 | 7.9/8.04 | 8.7/8.94 | NH: 3264w, CH: 3118m<br>—N=C<: 1615s, 1559m<br>CF: 1258s, 1211s, 1150s |
| 5 | $CF_3(CF_2)_6CH_2(C_4H_7)N$— | 87 | 144–145$^{3)}$/1 | 9.5/9.32 | 11.9/11.79 | CH: 2967m, 2879m<br>—N=C<: 1560s, 1493m<br>CF: 1242s, 1211s, 1149s |
| 6 | $CF_3(CF_2)_6CH_2(C_8H_{17})N$— | 71 | 144–147$^{3)}$/0.2 | 8.6/8.50 | 10.7/10.75 | CH: 2957m, 2860m<br>—N=C<: 1558s, 1494m<br>CF: 1243s, 1211s, 1150s |
| 7 | $CF_3(CF_2)_6CH_2(C_{12}H_{25})N$— | 67 | 160–162$^{3)}$/0.1 | 7.9/7.83 | 10.0/9.91 | CH: 2929m, 2858m<br>—N=C<: 1560s, 1493m<br>CF: 1243s, 1211s, 1150s |
| 8 | $CF_3(CF_2)_6CH_2(C_6H_5)N$— | 55 | 75–76 | 9.2/8.99 | 11.2/11.38 | CH: 3068m, 1612m<br>—N=C<: 1559s, 1491m<br>CF: 1243s, 1211s, 1150s |
| 9 | $CF_3(CF_2)_6CH_2(C_6H_{11})N$— | 77 | 60–61 | 8.7/8.91 | 11.4/11.27 | CH: 2935w, 2860m<br>—N=C<: 1561s, 1492m |

TABLE 2-continued

Characteristic values of 6-perfluoro alkylamino-1,3,5-triazine-2,4-dichloride

| Example | Substituent in 6 place | Yield (%) | Melting point (° C.) | $N^{1)}$ (%) | $C^{1)}$ (%) | IR characteristic absorption[2] (cm$^{-1}$) |
|---|---|---|---|---|---|---|
| 10 | $CF_3(CF_2)_9CH_2(C_4H_7)N$— | 65 | 55–65 | 7.6/<br>7.46 | 9.7/<br>9.44 | CF: 1245s, 1207s, 1147s<br>CH: 2967w, 2879m<br>—N=C<: 1560s, 1493m<br>CF: 1244s, 1210s, 1149s |

[1])Analyzed by Kjeldahl method; upper row: observed value; lower row: calculated value
[2])w: weak peak strength; m: medium peak strength; s: strong peak strength
[3])upper row: distillation temperature (° C.); lower row: degree of vacuum (Torr)

EXAMPLES 11–18

Solubility of 6-perfluoro alkylamino-1,3,5-triazine-2,4-dithiol to various solvents are shown in Table 4.

TABLE 3

Characteristic values of 6-perfluoro alkylamino-1,3,5-triazine-2,4-dithiol

| Example | Substituent in 6 place | Melting point (° C.) | $UV^{1)}$ | $SH^{2)}$ (%) | $N^{2)}$ (%) | IR characteristic absorption[3] (cm$^{-1}$) |
|---|---|---|---|---|---|---|
| 1 | $CF_3(CF_2)CH_2NH$— | 146–148 | 227/<br>2.81 | 22.5/<br>22.63 | 192/<br>19.17 | NH: 3245w, CH: 2946m<br>—NHCS—: 1595s, 1523m<br>CF: 1197s, 1157s |
| 2 | $CF_3(CF_2)_6CH_2NH$— | 246–248 | 296/<br>2.96 | 12.3/<br>12.19 | 10.1/<br>10.33 | NH: 32067w, CH: 2946m<br>—NHCS—: 1592s, 1523m<br>CF: 1209s, 1148s |
| 3 | $CF_3(CF_2)_8CH_2NH$— | — | 270/<br>2.83 | 9.9/<br>10.30 | 9.1/<br>8.72 | NH: 3274w, CH: 3120m<br>—NHCS—: 1633s, 1581m<br>CF: 1236s, 1208s, 1150s |
| 4 | $CF_3(CF_2)_9CH_2NH$— | — | 270/<br>2.77 | 9.6/<br>9.56 | 7.9/<br>8.09 | NH: 3261w, CH: 3120m<br>—NHCS—: 1616s, 1558m<br>CF: 1248s, 1207s, 1150s |
| 5 | $CF_3(CF_2)_6CH_2(C_4H_7)N$— | 217–219 | 270/<br>2.83 | 11.2/<br>11.05 | 9.1/<br>9.36 | CH: 2965m 2879m<br>—NHCS—: 1593s, 1495m<br>CF: 1242s, 1211s, 1149s |
| 6 | $CF_3(CF_2)_6CH_2(C_8H_{17})N$— | 146–148 | 270/<br>2.81 | 10.3/<br>10.11 | 8.7/<br>8.56 | CH: 2931m, 2861m<br>—NHCS—: 1591s, 1496m<br>CF: 1278s, 1207s, 1149s |
| 7 | $CF_3(CF_2)_6CH_2(CH_{12}H_{25})N$— | 117–118 | 270/<br>2.77 | 9.4/<br>9.31 | 7.8/<br>7.89 | CH: 2928m, 2857m<br>—NHCS—: 1588s, 1498m<br>CF: 1238s, 1200s, 1143s |
| 8 | $CF_3(CF_2)_6CH_2(C_6H_5)N$— | 125–127 | 285/<br>2.89 | 10.9/<br>10.70 | 9.3/<br>9.06 | CH: 3068m, 1612m<br>—NHCS—: 1558s, 1494m<br>CF: 1243s, 1211s, 1150s |
| 9 | $CF_3(CF_2)_6CH_2(C_6H_{11})N$— | 119–120 | 270/<br>2.84 | 10.2/<br>10.59 | 8.8/<br>8.97 | CH: 2942m, 2866m<br>—NHCS—: 1576s, 1535m<br>CF: 1245s, 1207s, 1147s |
| 10 | $CF_3(CF_2)_9CH_2(C_4H_7)N$— | 223–224 | 270/<br>2.74 | 8.8/<br>8.86 | 7.5/<br>7.51 | CH: 2937m, 2859m<br>—NHCS—: 1588s, 1539m<br>CF: 1242s, 1212s, 1150s |

[1])upper row: peak wavelength (nm); lower row: ×10$^{-4}$ (mol/L)
[2])upper row: observed value; lower row: calculated value (N and SH were respectively analyzed by Kjeldahl method and Ag-Volhalt method.
[3])w: weak peak strength; m: medium peak strength; s: strong peak strength

TABLE 4

Solubility of 6-perfluoro alkylamino-1,3,5-triazine-2,4-dithiol

| | | Solvents | | | | |
|---|---|---|---|---|---|---|
| Example | Substituent in 6 place | Water | Ethanol | Toluene | Acetic ether | MEK |
| 11 | $CF_3(CF_2)_6CH_2NH-$ | ○ | ○ | Δ | Δ | ○ |
| 12 | $CF_3(CF_2)_6CH_2(C_4H_7)N-$ | ○ | ○ | ○ | ○ | ◉ |
| 13 | $CF_3(CF_2)_6CH_2(C_6H_{11})N-$ | ○ | ○ | ○ | ○ | ◉ |
| 14 | $CF_3(CF_2)_9CH_2(C_4H_7)N-$ | ○ | ○ | ○ | ○ | ◉ |
| Comparative example | $CF_3(CF_2)_6C_6H_4NH-$ | Δ | Δ | X | Δ | Δ |

X: did not solved;
Δ: slightly solved (1 wt % or less);
○: sufficiently solved (1–10 wt %);
◉: excellently solved (10 wt % or more)

As seen from the above Table 4, all examples of the present invention have higher solubility than the comparative example, because substituents of examples have a higher flexing property than that of the comparative example. Accordingly, it is understood that the triazine thiol derivative having a perfluoro group of the present invention is effective as a surface treating agent.

In Table 5 below, there is shown the effectiveness of 6-perfluoro alkylamino-1,3,5-triazine-2,4-dithiol of examples of the present invention by comparing the dissociation constants, oxidation potential and critical micelle concentration with those of the comparative example.

TABLE 5

Dissociation constant, oxidation potential and critical micelle concentration of 6-perfluoro alkylamino-1,3,5-triazine-2,4-dithiol

| Example | Substituent in 6 place | pKa1 | pKa2 | Oxidation potential (V vs. $Ag^+/Ag$) | Critical micelle concentration (mol/L) |
|---|---|---|---|---|---|
| 15 | $CF_3(CF_2)_6CH_2NH-$ | 8.1 | 10.3 | 0.62 | $2.1 \times 10^{-3}$ |
| 16 | $CF_3(CF_2)_6CH_2(C_4H_7)N-$ | 7.4 | 10.4 | 0.46 | $2.1 \times 10^{-5}$ |
| 17 | $CF_3(CF_2)_6CH_2(C_6H_{11})N-$ | 6.2 | 10.6 | 0.78 | $5.6 \times 10^{-5}$ |
| 18 | $CF_3(CF_2)_9CH_2(C_4H_7)N-$ | 7.5 | 9.8 | 0.56 | $1.1 \times 10^{-5}$ |
| Comparative example | $CF_3(CF_2)_6C_6H_4NH-$ | 8.3 | 10.7 | 0.90 | $2.2 \times 10^{-2}$ |

With respect to the dissociation constants ($pKa_1$, $pKa_2$), which may function as a yardstick for reactivity, all the examples of the present invention have lower dissociation constants than the comparative example. Accordingly, it is understood that the triazine thiol derivative having a perfluoro group of the present invention has an excellent reactivity. With regard to the oxidation potential which functions as a yardstick for easiness of tribological polymerization and electrolytic polymerization, each example has a lower oxidation potential than the comparative example. This means that an oxidative polymerization of the triazine thiol derivative having a perfluoro group according to the present invention is easier than that of the comparative example. Further, the critical micelle concentration of every example is lower than that of the comparative example. This means that micelle formation is easier in the examples and thus, the triazine thiol derivative having a perfluoro group according to the present invention has an excellent surface activity. Since it is assumed that those substances which have excellent surface activity has more regularly arranged molecules in the resulting products, it is suggested that a film of the triazine thiol derivative having a perfluoro group according to the present invention is minute and thus, excellent in corrosion resistance.

EXAMPLES 19–22

Dipping Treatment

An Na salt of each 6-perfluoro alkylamino-1,3,5-triazine-2,4-dithiol shown in Table 6 below was dissolved in water at a concentration of $1 \times 10^{-3}$ mol/L and then, a plate (3×6× 0.2 mm) of iron, copper, nickel and silver (silver coated plate) were dipped therein at 70° C. for 30 minutes. In this connection, these metals were subjected to preliminary treatment by conducting ultrasonic degreasing for 3 minutes in trichloroethylene to remove deposits and the like, and kept in new trichloroethylene until the actual use. Surface treating performance with respect to each metal was evaluated though a contact angle of water and an eluting potential of the metal which was obtained from the anodic polarization curve [electrolyte: an aqueous solution of $(NaPo_3)_6$ of 0.1 M]. The results are also shown in Table 6. The contact angle shows whether water repellency was given to the metal surface and, the elution potential functions as a yardstick for thickness and corrosion resistance of a film formed on each metal. The larger contact angle indicates the higher water repellency, and the higher elution potential means the thicker film with superior corrosion resistance. Although effects of the fluorine group are seen in both of examples 19–22 and the comparative example, the examples of the present invention exhibited greater effects in both contact angle and elution potential than the comparative example. Accordingly, it is said that the reactivity with a metal surface as well as the thickness of a formed film of the examples are superior to those of the comparative example.

GPC (gel permeation chromatograph). The results are also shown in Table 7. The molecular weight measured in the comparative example shows that the dissolved compound

TABLE 6

Dipping treatment of metals with use of 6-perfluoro alkylamino-1,3,5-triazine-2,4-dithiol

| Example | Substituent in 6 place | Evaluated Property | Iron | Copper | Nickel | Silver |
|---|---|---|---|---|---|---|
| 19 | $CF_3(CF_2)_5CH_2NH-$ | Contact angle (°) | 113 (56) | 121 (67) | 117 (82) | 121 (68) |
|  |  | Eluting potential (V vs SCE) | 1.5 (1.4) | 1.7 (−0.2) | 1.75 (1.5) | 1.1 (0.3) |
| 20 | $CF_3(CF_2)_6CH_2(C_4H_7)N-$ | Contact angle (°) | 114 (56) | 120 (67) | 119 (82) | 121 (68) |
|  |  | Eluting potential (V vs SCE) | 1.6 (1.4) | 1.9 (−0.2) | 1.9 (1.5) | 1.5 (0.3) |
| 21 | $CF_3(CF_2)_6CH_2(C_6H_{11})N-$ | Contact angle (°) | 116 (56) | 121 (67) | 120 (82) | 120 (68) |
|  |  | Eluting potential (V vs SCE) | 1.6 (1.4) | 1.9 (−0.2) | 1.9 (1.5) | 1.6 (0.3) |
| 22 | $CF_3(CF_2)_9CH_2(C_4H_7)N-$ | Contact angle (°) | 112 (56) | 120 (67) | 121 (82) | 120 (68) |
|  |  | Eluting potential (V vs SCE) | 1.6 (1.4) | 1.9 (−0.2) | 1.9 (1.5) | 1 (0.3) |
| Comparative example | $CF_3(CF_2)_6C_6H_4NH-$ | Contact angle (°) | 90 (56) | 114 (67) | 110 (82) | 106 (68) |
|  |  | Eluting potential (V vs SCE) | 1.4 (1.4) | 0.2 (−0.2) | 1.6 (1.5) | 0.5 (0.3) |

EXAMPLES 23–26
Tribological Treatment

An Na salt of each 6-perfluoro alkylamino-1,3,5-triazine-2,4-dithiol shown in Table 7 below was dissolved in an ordinarily used water based lubricant (an emulsion type lubricant comprising of extreme pressure inhibitor, oiliness improver, emulsifying agent, forming inhibitor and the like) at a concentration of $5\times10^{-3}$ mol/L and used as the lubricant. A circular cutting of a metal column (30×30 φmm) was conducted with use of an engine lathe (emcomat-7 manufactured by Austria Mayer Co. Ltd.) at a rate of 1450 rpm, while poring the above-prepared lubricant at a rate of 3 cm³/min. The cuttings obtained during the machining were gathered to amount to 2 g. The cuttings were well washed with water and methanol, and then dried. The thus-obtained cuttings were dipped in 20 ml of THF for 12 hours at a temperature of 40° C., so that the compounds which had adhered to the surface of the cuttings were dissolved therein. The molecular weight as well as the amount of film of respective dissolved compounds were measured with use of was a dimer or a trimer, while each molecular weight measured in the examples 23–26 indicates that the dissolved compound was a considerably large polymer. The amount of film in the comparative example was very little and further, the amounts of film in the examples of the present invention are lager than that in the comparative example by a hundred times or more. The larger the molecular weight is, the higher the strength of the film. In addition, a larger amount of film means a more excellent corrosion resistance.

TABLE 7

Tribological treatment of metals with use of 6-perfluoro alkylamino-1,3,5-triazine-2,4-dithiol

|  |  | Number-average molecular weight | | Amount of film (µg/g) | |
|---|---|---|---|---|---|
| Example | Substituent in 6 place | Iron column | Copper column | Iron column | Copper column |
| 23 | $CF_3(CF_2)_6CH_2NH-$ | 3,300 | 17,000 | 1.5 | 5.4 |
| 24 | $CF_3(CF_2)_6CH_2(C_4H_7)N-$ | 8,200 | 26,000 | 1.6 | 6.4 |
| 25 | $CF_3(CF_2)_6CH_2(C_6H_{11})N-$ | 9,300 | 31,000 | 1.9 | 6.9 |
| 26 | $CF_3(CF_2)_9CH_2(C_4H_7)N-$ | 9,800 | 36,000 | 2.1 | 7.1 |
| Comparative example | $CF_3(CF_2)_6C_6H_4NH-$ | 1,500 | 3,200 | <0.1 | <0.1 |

EXAMPLES 27–30
Electrolytic Polymerization Treatment

An Na salt of each 6-perfluoro alkylamino-1,3,5-triazine-2,4-dithiol shown in Table 8 below was dissolved in water at a concentration of $5\times10^{-3}$ mol/L to prepare an electrolyte. The thus-obtained electrolyte was charged into an electrolytic cell (K. Mori:), and while using a cathode of iron plate or SUS 304 plate (30×60×0.2 mm) and an anode of platinum plate, electrolytic polymerization was conducted for 10 minutes at a current density of 0.1 mA/cm² and a temperature of 40° C. After this electrolytic polymerization, the iron plate and SUS 304 plate used as the cathode were washed with methanol to remove unreacted substances, and then dried.

After that, the iron plate and SUS 304 plate were dipped in 20 ml of THF for 12 hours at a temperature of 40° C., so that the compounds which had adhered to the surface of each plate were dissolved therein. The molecular weight as well as the amount of film of respective dissolved compounds were measured with use of GPC (gel permeation chromatograph). The results are also shown in Table 8. The examples of this invention show superior results in both number-average molecular weight and amount of film than the comparative example by ten to hundred times. Accordingly, it would be understood that the material structure of the present invention leads to a high reactivity.

TABLE 8

Electrolytic polymerization treatment of metals with use of 6-perfluoro alkylamino-1,3,5-triazine-2,4-dithiol

| | | Number-average molecular weight | | Amount of film ($\mu$g/cm²) | |
|---|---|---|---|---|---|
| Example | Substituent in 6 place | Iron plate | SUS 304 plate | Iron plate | SUS 304 plate |
| 27 | $CF_3(CF_2)_6CH_2NH-$ | 109,000 | 110,000 | 2.3 | 6.6 |
| 28 | $CF_3(CF_2)_6CH_2(C_4H_7)N-$ | 280,000 | 340,000 | 6.7 | 12.6 |
| 29 | $CF_3(CF_2)_6CH_2(C_6H_{11})N-$ | 310,000 | 350,000 | 6.8 | 13.2 |
| 30 | $CF_3(CF_2)_9CH_2(C_4H_7)N-$ | 320,000 | 330,000 | 6.3 | 13.6 |
| Comparative example | $CF_3(CF_2)_6C_6H_4NH-$ | 9,800 | 12,000 | 0.3 | 0.6 |

As described above, the triazine thiol derivative having a perfluoro group according to the present invention is excellent in reactivity, solubility and surface activity and thus, industrial fields and uses to which the triazine thiol derivative having a perfluoro group of the present invention is applicable has been greatly enlarged. A film for metal surface formed of the triazine thiol derivative having a perfluoro group according to the present invention has properties such as corrosion resistance, lubricity, anti-staining property, nontackiness, anti-fogging property, anti-icing property and the like. Accordingly, it is applicable to various products which requires these properties (for instance, materials for connector, metal gears, metal products for decoration, metallic mirrors, metallic molds, hard discs, magnetic tapes, hands of watch, metallic tableware and the like). Moreover, since the film of the triazine thiol derivative having a perfluoro group according to the present invention has a surface of low free energy, it is effectively used in complexing with various fluoride, thereby contributing fluoridation of many metals and electric conductors.

Although the invention has been described with reference to specific preferred embodiments, they were given by way of examples only and thus, it should be noted that various changes and modifications may be made on them without departing from the scope of the present invention as defined by the appended claims.

What is claimed is:

1. A triazine thiol derivative having a perfluoro group represented by the following chemical formula (1):

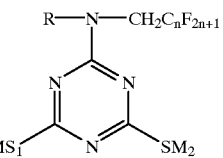

wherein "n" is an integer of 1–12, "R" is represented by the following general formula;

$C_mH_{2m+1}$ wherein m is an integer of 0–24, and $M_1$ and $M_2$ respectively represent a hydrogen atom (H) or an alkali metal.

2. A method for producing a triazine thiol derivative having a perfluoro group comprising preparation steps of:

(1) synthesizing a secondary amine having a perfluoro group;

(2) synthesizing a triazine dichloride having a perfluoro group from said secondary amine having a perfluoro group and cyanur chloride; and then (3) synthesizing a triazine thiol derivative having a perfluoro group from said triazine dichloride having a perfluoro group.

3. A method for producing a triazine thiol derivative having a perfluoro group comprising preparation steps of:

(1) synthesizing a secondary amine having a perfluoro group, wherein said secondary amine having a perfluoro group is prepared through a reaction represented by the following reaction formula;

$$RfCOOH + SO_2Cl_2 \longrightarrow RfCOCl \qquad (1\text{-}1)$$

$$RfCOCl + RNH_2 \longrightarrow RfCONHR \qquad (1\text{-}2)$$

$$RfCONHR \longrightarrow RfCH_2NHR \qquad (1\text{-}3)$$

wherein R is defined as in claim 1

(2) synthesizing a triazine dichloride having a perfluoro group from said secondary amine having a perfluoro group and cyanur chloride, said triazine dichloride having a perfluoro group is prepared through a reaction represented by the following reaction formula;

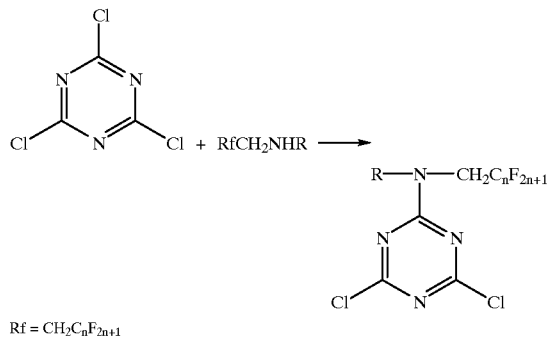

and then (3) synthesizing a triazine thiol derivative having a perfluoro group from said triazine dichloride having a perfluoro group, said triazine thiol derivative having a perfluoro group is prepared through a reaction represented by the following reaction formula;

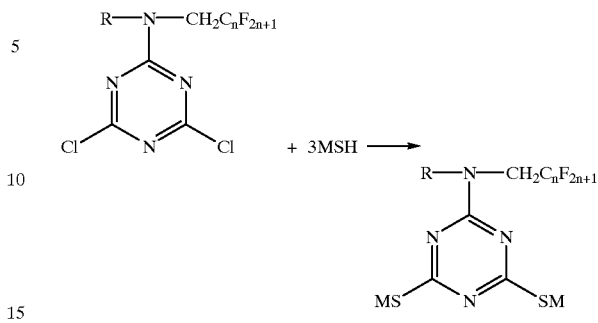

wherein R is defined as in claim 1.

4. A film for metal surface comprising a triazine thiol derivative having a perfluoro group as set forth in claim 1.

* * * * *